United States Patent [19]

Coffen

[11] 4,093,654

[45] June 6, 1978

[54] PRODUCTION OF PYRIDOXINE INTERMEDIATES FROM DIKETENE

[75] Inventor: David Llewellyn Coffen, Glen Ridge, N.J.

[73] Assignee: Hoffmann-La Roche Inc., Nutley, N.J.

[21] Appl. No.: 783,240

[22] Filed: Mar. 31, 1977

[51] Int. Cl.$^2$ .................................... C07C 103/133
[52] U.S. Cl. .................... 260/561 A; 260/307 R; 260/561 N; 260/561 HL
[58] Field of Search ............... 260/561 A, 561 N

[56] References Cited

U.S. PATENT DOCUMENTS

| | | | |
|---|---|---|---|
| 3,038,003 | 6/1962 | Fürst et al. | 260/561 A |
| 3,149,155 | 9/1964 | Seefelder | 260/561 A |
| 3,703,518 | 11/1972 | Inol et al. | 260/561 A |

*Primary Examiner*—Arthur P. Demers
*Attorney, Agent, or Firm*—Samuel L. Welt; Bernard S. Leon; George W. Johnston

[57] ABSTRACT

A process for the preparation of oxazoles, particularly 4-lower alkyl-5-cyanooxazoles, from diketene is disclosed.

2 Claims, No Drawings

PRODUCTION OF PYRIDOXINE INTERMEDIATES FROM DIKETENE

BACKGROUND OF THE INVENTION

Pyridoxine (vitamin $B_6$) is a well known vitamin normally used as an adjunct is prophylaxis and treatment of multiple vitamin B complex deficiencies. It is also used in dermatoses, neuromuscular and neurological diseases.

An important synthetic procedure for pyridoxine involves the use of 4-methyl-5-cyanooxazole as a key intermediate. A typical synthetic procedure is that of Kimel et al., disclosed in U.S. Pat. No. 3,250,778, wherein 4-methyl-5-cyanooxazole is condensed with a 4,7-dihydro-1,3-dioxepin followed by acid hydrolysis of the resultant product to form pyridoxine. However, there is a continuing search to find more efficient and economical methods of producing the 4-methyl-5-cyanooxazole intermediate. Prior methods of preparing this intermedate have involved either heating 4-methyloxazole-5-carboxamides with phosphorus pentoxide or utilizing conventional amide dehydrating agents, such as phosphorus oxyhalides, to form the corresponding amides.

It has now been found that oxazole intermediates, preferably 4-methyl-5-cyanooxazole, useful in pyridoxine (vitamin $B_6$) manufacture, may be prepared from diketene. Diketene is an inexpensive raw material and is presently used as such in vitamin A manufacture.

SUMMARY OF THE INVENTION

In accordance with the instant invention, it has been found that 4-methyl-cyanooxazole may be prepared as illustrated in the following reaction schemes:

"halide", "halite" denotes chlorine, bromine, iodine or fluorine.

As indicated hereinabove a compound of the formula:

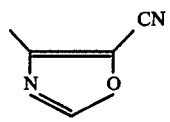

may be prepared in accordance with one of two reaction schemes shown hereinabove which form the immediate precursors of compound I, i.e., the 4-methyl oxazole-5-carboxamide, by employing diketene as the starting material.

Diketene, a compound of the formula:

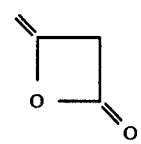

is reacted with an excess of ammonia to form a compound of the formula:

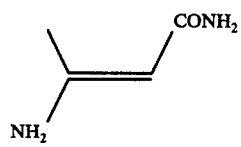

The reaction of compound II with ammonia may be

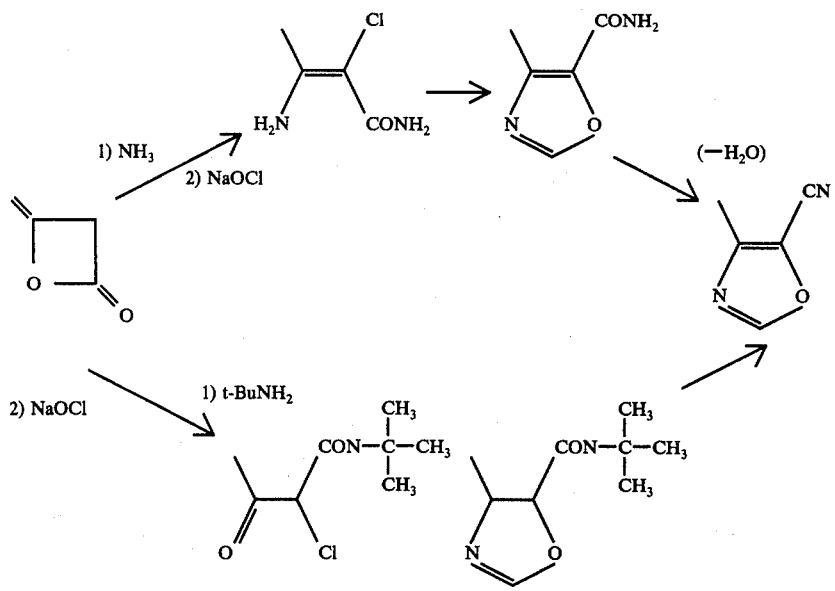

The instant invention provides to the art a method for the preparation of 4-methyl-5-cyanooxazole which is efficient and economical due to the low costs of the starting material.

DETAILED DESCRIPTION OF THE INVENTION

The term "alkali metal" as used herein denotes sodium, potassium, lithium. The expression "halogen", conducted in the presence or absence of a solvent, with the latter being preferred. When the reaction is carried out in the absence of a solvent, the diketene is slowly added to cold liquid ammonia. This reaction is generally carried out at atmospheric pressure in which case the reaction temperature will be at or near the boiling point of liquid ammonia. Although there is no limit to the molar excess of ammonia (as compared to diketene) that may be used, no practical advantage is gained by employing molar excesses greater than 4 or 5:1.

When solvents are employed for the foregoing reaction, ethers such as diethyl ether, dioxane, tetrahydrofuran (THF) and the like may be used.

Compound II is then transformed to a compound of the formula:

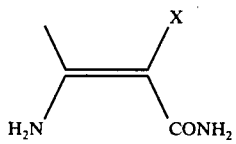

wherein X is halogen;
by treating compound III with a halogenating agent, preferably sodium hypochlorite, at a temperature ranging from about 5° C. to about 25° C., preferably about 10° C. The halogenation is generally carried out in an aqueous medium. As the chlorination proceeds, compound IV, being sparingly soluble in aqueous media, precipitates as it forms. Other halogenating agents that may be used in this reaction are aqueous calcium hypochlorite, aqueous N-bromosuccinimide, and halogen.

Compound IV is then transformed to a compound of the formula:

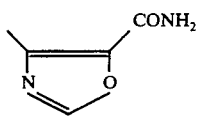

by treatment of the former with a mixture of ammonium formate, formic acid and formamide, optionally in the presence of a zinc halide, preferably zinc chloride. The reaction to form compound V is generally carried out at temperatures ranging from about 95° C., to about 140° C., preferably 120° C. Zinc halide, when employed, is generally used in amounts of from 0.001 mole to about 0.1 mole (based on compound IV).

Compound V may then be dehydrated to form a compound having the formula I. Compound V may be dehydrated by techniques conventional for the dehydration of a oxazole carboxamide to a cyanooxazole. Particularly preferred dehydrations are those disclosed in Chase U.S. Pat. No. 3,222,374 and Ser. No. 573,226, filed Apr. 30, 1975 to Coffen, the disclosure of which is incorporated herein by reference.

Compound V may also be prepared by acid hydrolysis of compound IV to form a ketone of the formula:

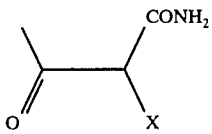

wherein X is halogen;
followed by conversion of said ketone to the oxazole. The hydrolysis step is generally carried out in an inert solvent, preferably diethyl ether, and at a temperature varying from about 25° C. to about 60° C. Acids that may be used in the hydrolysis are mineral acids such as $H_2SO_4$, HCl, HBr, $H_3PO_4$ and the like.

The conversion of compound VI to compound V is effected by treatment of the former compound with a mixture of ammonium formate, formic acid and formamide according to the procedures described hereinbefore.

An alternative procedure for preparing compound I employing diketene as the starting material involves treating said compound, in equimolar quantities, with t-butyl amine to form a compound of the formula:

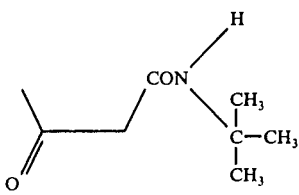

said reaction being conducted in an aqueous medium. The reaction is generally carried out at atmospheric pressure and a temperature ranging from about 5° C. to about 25° C.

Compound VII is then halogenated under acid conditions to form a compound of the formula:

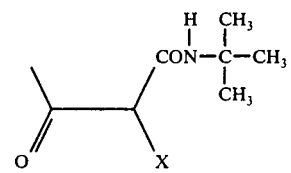

wherein X is halogen.

The halogenation of compound VII generally takes place in an aqueous medium at pH of from about 1 to about 5, to avoid the obtention of dihalogenated products or a mixture of mono and dihalogenated products. The halogenating agents may be selected from those mentioned hereinabove.

Compound VIII is then transformed to compound Va of the formula:

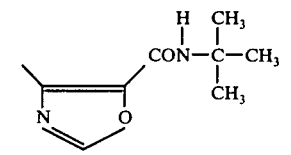

by treating the former with a mixture of ammonium or an alkali metal formate (preferably sodium formate), formamide, and formic acid. The transformation of compound VIII to compound Va is accomplished by heating at a temperature varying from about 80° C. to about 160° C.

An alternative means of effecting the transformation of compound VIII to compound Va consists of dispersing the above-mentioned reaction mixture in a hydrocarbon or other non-polar solvent (immiscible with the formamide-formic acid mixture) accompanied by heating the dispersed mixture to the reflux temperature of said solvent. The refluxing solvent, rather than being directly returned to the reaction mixture, is first conducted to a trap thus permitting the removal of water by azeotropic distillation. This water, which is formed during the reaction, has a deleterious effect on the yield of compound Va. Continuous removal of the water has been found to significantly improve the yields of compound Va.

Still further, the presence of the t-butyl group on the amide function of the oxazole solublizes the oxazole as formed into the non-polar phase of the reaction mixture. This solubilization reduces the extent to which oxazole is converted to undesirable imidazole by-product.

Solvents that may be employed in the conversion of compound VIII to compound Va, are the typically inert solvents, such as higher boiling alkanes, e.g., heptane, aromatic hydrocarbons such as benzene, toluene, xylene, halogenated hydrocarbons, such as chlorobenzene, and higher boiling ethers.

Compound Va may then be transformed to compound I by the dehydration procedures set forth hereinabove. Dehydration of compound Va is simplified by the fact that it is volatile, soluble and of low melting point. These characteristics make it particularly amenable to the Coffen dehydration procedure described in Ser. No. 573,226 (referred to hereinabove). Additionally, a by-product of the dehydration step, viz, isobutylene, can be used to regenerate both t-butylamine and sodium formate by combining said by-product with HCN in $H_2SO_4$ followed by basic hydrolysis of the resulting t-butylformamide.

The non-limiting examples which follow are illustrative of the instant invention. All temperatures are in degree centigrade.

EXAMPLE 1

Trans-α-Chloro-β-aminocrotonamide

About 200 ml of ammonia were condensed in a 500 ml flask cooled in a dry ice/acetone bath. Diketene (84 g, 1 mol) was added dropwise with stirring. An additional 100 ml of liquid ammonia was added and the mixture was left overnight during which the excess ammonia was allowed to evaporate. The solid β-aminocrotonamide was removed from the flask and left in the air for two hours to allow residual ammonia to escape. It was then transferred to a 3 l flask, dissolved in cold water (250 ml), and cooled to 10° with an ice/acetone bath. Aqueous sodium hypochlorite (5.25% solution, "Chlorox", 1500 ml, 1 mol) was added gradually with rapid mechanical stirring. The rate of addition was controlled so that the temperature of the reaction did not exceed 10°. When addition was completed, the product was collected, washed sparingly with cold water, and air-dried to give 80.3 g of colorless solid. Ether extraction of the aqueous filtrate afforded an additional 7.4 g of product giving a yield of 87.7 g (65.5%).

EXAMPLE 2

4-Methyloxazole-5-carboxamide

A solution of α-chloro-β-aminocrotonamide (1.34 g, 0.01 mol), ammonium formate (1.34 g), zince chloride (.3 g), formamide (3 ml), and formic acid (3 ml) was stirred and heated in an oil bath at 120° for 75 minutes. After being allowed to cool partially, water (3 ml) was added and the solution was cooled and scratched with a seed crystal of oxazole amide. It was then stored in the freezer overnight. The first crop of product (350 mg) was collected, washed with ethanol and air-dried. A second crop, also 350 mg, was obtained by concentrating the filtrate under reduced pressure followed by addition of more water (1 ml) to keep inorganic salts in solution. The combined crops were vacuum sublimed to give 680 mg (54%) of colorless oxazole amide.

EXAMPLE 3

2-Chloroacetoacetamide

A mixture of α-chloro-β-aminocrotonamide (4 g), and concentrated HCl (4 ml), in ether (4 ml) was stirred for 1 hour. The mixture was then diluted with $CH_2Cl_2$ (20 ml), dried with $Na_2SO_4$ and decanted. The solid was thoroughly washed several times with ether and the combined organic layers evaporated. The wet residue was taken up to either, diluted with benzene and again evaporated to give 3.8 g (94.3%) of pale yellow ketone.

EXAMPLE 4

2-Chloro-N-tert-butylacetoacetamide

Diketene (42 g, 0.5 mol) was mixed with ca. 200 ml of ice and water in a 2 l., 3-neck flask. A solution of t-butylamine (37.5 g, 0.5 mol) in water (150 ml) was added gradually with stirring and more ice was added as needed to keep the reaction at or below 20°. The solution was stirred for 20 minutes after completing the addition, acidified with concentrated HCl (400 ml), and cooled to 10° with an ice/acetone bath. Aqueous sodium hypochlorite ("Chlorox", 750 ml, 0.5 mol) was then added dropwise with rapid mechanical stirring. The product was filtered out, washed with water and air-dried for several hours to give 78.5 g (81.8%) of colorless solid.

EXAMPLE 5

N-tert-Butyl-4-methyloxazole-5-carboxamide

A mixture of 2-chloro-N-tert-butylacetoacetamide (19.2 g, 0.1 mol) and sodium formate (8.1 g, 0.12 mol) in formamide/formic acid mixture (35 ml of former diluted to 50 ml with latter) was immersed in an oil bath preheated to 160° and stirred at this temperature for 15 minutes. Sodium chloride precipitated during the reaction. After cooling, the reaction mixture was diluted with water and made basic with aqueous NaOH. It was then extracted four times with $CH_2Cl_2$. The combined extracts were washed with water and the aqueous layer was reextracted twice with $CH_2Cl_2$. The combined $CH_2Cl_2$ extracts were dried and evaporated. The resulting syrup was taken up in a small volume of $CH_2Cl_2$ and scratched. The solid was collected, washed with $CH_2Cl_2$ and air-dried giving 1.0 g of a by-product identified as an imidazole. The filtrate was evaporated and the residue distilled in vacuum. The oxazole distilled as a colorless liquid with b.p. 96°10.2 mm which, upon standing, formed a crystalline solid, 9.73 g (53.4%). The pot residue was taken up in $CH_2Cl_2$/ether and stored giving a further 1.4 g of imidazole by-product.

An analytical sample of the oxazole was recrystallized from ether/hexane to give colorless crystals with m.p. 72°–6°.

EXAMPLE 6

To the mixture of reagents described in Example 5, (same scale), toluene (200 ml) was added and the resulting two-phase mixture was heated to reflux with vigorous stirring. Water and formic acid were allowed to collect in a trap and 17 ml collected during 5 hours. The reaction mixture was cooled and the toluene layer decanted off and washed with water (ca. 50 ml). The wash water was added to the formamide layer which was then made basic with aqueous $Na_2CO_3$. This aqueous solution was then extracted twice with toluene and the toluene extracts were combined with the decanted toluene layer. During the first extraction of the aqueous layer, a solid formed which was collected, washed and dried to give 1.9 g of an imidazole by-product. The combined toluene layers were dried and the toluene evaporated to give 15.2 g of crude, solid oxazole. Purification by vacuum distillation gave 10.94 g (60%) of colorless, crystalline oxazole.

EXAMPLE 7

4-Methyl-5-cyanooxazole

A quartz column with packable dimensions of 1 × 40 cm was packed with 10% $P_2O_5$ on silica gel. The column was heated with a heating tape to give an internal temperature of 425°. N-tert-butyl-4-methyloxazole-5-carboxamide (19 g) was distilled upwards into the column under 35 mm pressure and with an oil bath at 180° to heat the flask containing the amide. The vapors exiting at the top of the column were trapped in two consecutive traps cooled with ice/acetone and liquid nitrogen bath respectively. Most of the nitrile was collected in the first trap. The material in the second trap consisted of isobutylene (5.0 g, 85%) which was identified by gc/ms analysis and a small amount (ca. 1 g) of nitrile. The nitrile from the two traps was combined, diluted with $CH_2Cl_2$, dried with $Na_2SO_4$, and vacuum distilled at aspirator pressure to give 8.75 g (77.6%) of pure nitrile.

EXAMPLE 8

Following the procedure of Example 7, the t-butyl oxazoleamide was dripped onto the top of the headed column from a heated side-arm addition funnel. From 33.8 g of oxazoleamide added, the following was obtained:
  Starting material, 15.35 g (45.4%)
  4-Methyl-5-cyanooxazole, 6.36 g (58% based on oxazoleamide consumed)
  Isobutylene, 6 g, (100% based on oxazoleamide consumed)
  4-Methyloxazole-5-carboxamide, 0.94 g.

EXAMPLE 9

A solution of N-tert-butyl oxazoleamide (18.2 g, 0.1 mole) and phosphorus pentachloride (25.0 g, 0.12 mole) in chloroform (150 ml) was heated at reflux for 30 hours. The solvent was removed by distillation at atmospheric pressure and the residue was distilled rapidly without fractionation at approximately 0.1 mm. The distillate was redistilled with fractionation through a Vigreux column giving 9.25 g of a mixture of cyanooxazole and phosphorus oxychloride in one fraction and 6.3 g of recovered N-tert-butyl oxazoleamide in another. The fraction containing the cyanooxazole was analyzed qualitatively by infrared and nmr spectroscopy and quantitatively by ultraviolet spectroscopy. By the last method it was found to contain 45.2% cyanooxazole. This corresponds to a yield of 4.18 g or 59.2% on the 11.9 g of amide consumed.

EXAMPLE 10

Preparation of 4-Methyloxazole-5-carboxamide from 2-Chloro-3-oxobutyramide

A mixture of 2-chloro-3-oxobutyramide (1.35 g, 0.01 mole), ammonium formate (1.35 g), formamide (3 ml) and formic acid (3 ml) was heated in a 125° oil bath for 1 hour. The solution was cooled, scratched to induce crystallization, and chilled for several hours. The product was collected, washed with ethanol and air-dried to give 700 mg of an off-white solid. This was vacuum sublimed to give 660 mg (52.3%) of colorless amide. In another experiment carried out in the same way, the yield of sublimed amide was 720 mg (57%). The identity of the amide was verified with its ir spectrum.

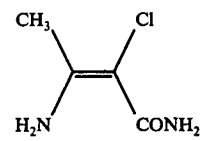

I claim:
1. A compound of the formula:

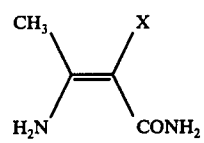

wherein X is halogen.

2. The compound of claim 1 wherein said compound is: